(12) United States Patent
Otten, III et al.

(10) Patent No.: US 8,882,274 B1
(45) Date of Patent: Nov. 11, 2014

(54) LASER WAVEFRONT CHARACTERIZATION

(76) Inventors: Leonard John Otten, III, Placitas, NM (US); Paul Harrison, Albuquerque, NM (US); Desirae L. Cuevas, Albuquerque, NM (US); Paul Fournier, Albuquerque, NM (US)

( * ) Notice: Subject to any disclaimer, the term of this patent is extended or adjusted under 35 U.S.C. 154(b) by 1018 days.

(21) Appl. No.: 12/536,333

(22) Filed: Aug. 5, 2009

(51) Int. Cl.
*A61B 3/10* (2006.01)
*A61B 3/00* (2006.01)

(52) U.S. Cl.
CPC .............. *A61B 3/1015* (2013.01); *A61B 3/0008* (2013.01)
USPC ......... 351/221; 351/210; 351/205; 250/338.1

(58) Field of Classification Search
CPC .............................. A61B 3/0008; A61B 3/1015
USPC ......... 351/200, 204, 205, 210, 212–216, 246, 351/247; 250/338.1
See application file for complete search history.

(56) References Cited

U.S. PATENT DOCUMENTS

| | | | |
|---|---|---|---|
| 4,773,063 A * | 9/1988 | Hunsperger et al. | 398/87 |
| 6,464,357 B1 * | 10/2002 | Otten et al. | 351/212 |
| 7,232,999 B1 * | 6/2007 | Otten et al. | 250/338.1 |

FOREIGN PATENT DOCUMENTS

WO    WO 03/002024    *  1/2003  .................... 351/212

* cited by examiner

*Primary Examiner* — Huy K Mai
(74) *Attorney, Agent, or Firm* — Rodey, Dickason, Sloan, Akin & Robb, P.A.; DeWitt M. Morgan

(57) ABSTRACT

The device and method of the present invention are useful for determining the characteristics of an infrared wavefront. The present invention involves positioning a beam of light containing the infrared wavefront to be characterized onto a distorted grating, using the grating to produce a plurality of images, determining the infrared wavefront from the plurality of images and analyzing the infrared wavefront for features that characterize the infrared wavefront.

9 Claims, 25 Drawing Sheets

Figure 22(a) – $W_{20} = 1\lambda$  Figure 22(b) – $W_{20} = 3\lambda$

Gratings distorted according to the equation describing $\Delta_x(x,y)$, with $R = 20d$, and the grating origin $(0,0)$ is at the center of the circle aperture.

US 8,882,274 B1

LASER WAVEFRONT CHARACTERIZATION

GOVERNMENT RIGHTS CLAUSE

This invention is made with U.S. Government support under Contract F29601-02-C-0130 awarded by the U.S. Air Force. The U.S. Government has certain rights in the invention.

CLAIM FOR PRIORITY

A claim for priority is made in this application for copending application Ser. No. 11/820,651 filed on Jun. 19, 2007 which, in turn is a continuation of application Ser. No. 10/903,095 filed Jul. 30, 2004, now U.S. Pat. No. 7,232,999 B1 which, in turn, claims the priority of the provisional application Ser. No. 60/491,076 filed on Jul. 30, 2003.

FIELD OF THE INVENTION

This invention relates to a distorted grating based wavefront sensor (DGWFS) developed to measure wavefronts of, for instance, infrared radiation. The invention has been shown to produce accurate wavefront data while simultaneously producing accurate tip-tilt data along with the higher order terms in a very rugged configuration.

BACKGROUND OF THE INVENTION

With infrared lasers now being developed for a wide range of applications there is a need for diagnostics instrumentation for characterizing performance and to serve as the input to a dynamic active beam brightness correction system. Many applications impose unique restrictions that limit the application of conventional laser diagnostics. Size, weight, robustness, and unattended operations all make conventional measurement sensors difficult to adapt. Ideally, an infrared laser diagnostics suite would encompass small sensors that were capable of measuring simultaneously multiple laser characteristics and require minimum modification for adaptation to a wide range of applications.

SUMMARY OF THE INVENTION

The technology base for this laser sensing combines phase diversity and wavefront curvature wavefront sensing techniques. In both of these approaches, the intensity is measured in two planes through which the wavefront propagates. The difference between these planes gives a measure of the axial intensity gradient. Solving of a differential equation, the intensity transport equation, provides a non-iterative solution to the wavefront reconstruction. The inventors have demonstrated the distorted grating wavefront sensing technique non-iterative wavefront reconstruction in simulations with high levels of scintillation, under thermal heating conditions and using extended sources such as will be found when looking at an infrared laser beam.

The invention uses a wavefront sensor based on wavefront curvature. Investigated for a number of years, wavefront curvature requires the collection of two or more images of the intensity distribution in two spatially separated planes in the vicinity of the entrance pupil of the wavefront sensing instrument with a known wavefront aberration introduced between the images. These images must be measured in the time scale of distortion being compensated, e.g., the sensing must be done while the disturbance is effectively stationary. A technique that can collect the two images simultaneously is therefore required.

In the wavefront sensor of the present invention, the difference between the intensities of two image planes with a known aberration (e.g., a focus shift or other aberrations) indicates the position, direction, and magnitude of the aberration. The shape of the wavefront is computed from the difference matrix through a matrix multiplication with a pre-computed Green's function. It is therefore critical that the multiple frames are accurately and consistently registered, the detector is well characterized and the introduced aberration is a controlled function. Preferably, the wavefront sensor would record the multiple images on a single detector.

The basis for the wavefront curvature technique can be understood by considering the propagation of a wavefront between two planes. Those regions of the wavefront that are concave on the first plane converge as they propagate toward the second plane. Those regions of the wavefront that are convex on the first plane diverge as they propagate toward the second plane. The intensity on the second plane is increased, or reduced, compared to the first plane. A measurement of the intensity gradient along the optical axis provides indications of the local wavefront curvature.

The technology that creates the multiple images is based on local displacement of lines in a diffraction grating used to introduce arbitrary phase shifts into wavefronts diffracted into the non-zero orders, a principle that is well known in the art. A quadratic displacement function is used to alter the optical transfer function associated with each diffraction order such that each order has a different degree of defocus. This modification to produce a distorted grating allows it to serve as a beam splitter while producing simultaneous images of multi object planes on a single image plane.

A quadratic displacement function is used to alter the optical transfer function associated with each diffraction order such that each order has a different degree of defocus. This 'defocus grating' enables the simultaneous imaging of multiple object planes on a single image plane, using a single camera. The technique preserves the resolution of the input optics in each of the images.

The above described technique is useful and effective to characterize the wavefront of a laser of any wavelength, including, but not limited to the infrared wavelengths.

OBJECTS OF THE INVENTION

It is an object of the present invention to use a distorted grating wavefront sensor to measure the wavefront characteristics of an infrared laser.

It is further an object of the invention to provide for a wavefront sensor which characterizes the Zernike terms of a wavefront.

It is still another object of the present invention to provide for an infrared laser wavefront sensor that is not sensitive to increased background noise from thermal heating of the optical elements.

It is still a further object of the invention to provide for a transmissive refractive grating for achieving the previous objects.

It is still a further object of the invention to provide for a reflective grating for achieving the previous objects.

It is yet an additional object of the present invention to provide a wavefront measurement of a high power infrared laser.

It is still a further object of the present invention to provide a wavefront measurement of an infrared laser under severe environments.

It is yet a further object of the present invention to provide a wavefront measurement of an infrared laser that has strong amplitude modulations (from 0 to beyond detector saturation).

It is yet a further object of the present invention to provide a wavefront measurement of an infrared laser that has strong phase modulations (greater than 360°).

It is finally an object of the present invention to provide a wavefront measurement of an infrared laser over the complete area of the laser beam.

The foregoing and further objects are apparent from the specification and drawings herein.

DESCRIPTION OF THE PREFERRED EMBODIMENT

Figure 1:
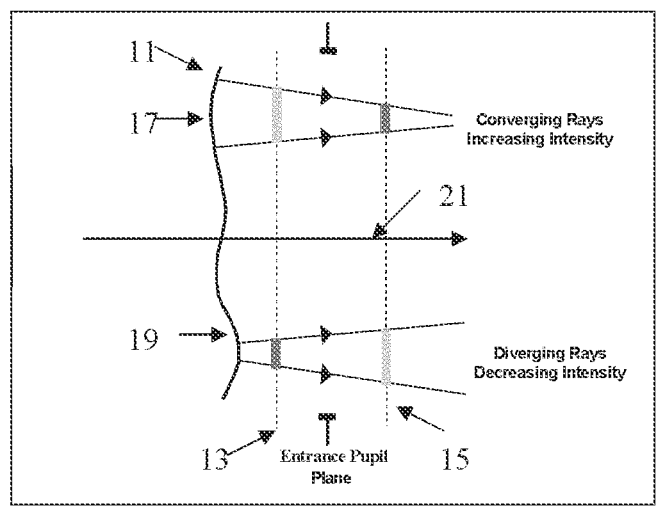
FIG. 1 illustrates the measurements made at two image planes with a known aberration, which are required for a wavefront curvature sensor.

The use of a distorted grating wavefront sensing for determining the characteristics of a laser is described below. With reference to FIG. 1, in order for such a wavefront sensor to work the difference between the intensities of the wavefront with a known aberration 11 at a first image plane 13 and a second image plane 15 is taken. This difference in the intensities indicates the position, direction, and magnitude of the aberration to be corrected. The shape of the wavefront is computed from the difference matrix through a matrix multiplication with a pre-computed Green's function. It is therefore critical that the multiple frames are accurately and consistently registered, the detector is well characterized and the introduced aberration is a controlled function. Preferably, the wavefront sensor would record the multiple images on a single detector.

FIG. 1 illustrates the basics for the wavefront curvature technique by considering the propagation of a wavefront 11 between two planes 13 and 15. Those regions 17 of the wavefront 11 that are concave on the first plane converge as they propagate toward the second plane 15. Similarly, those regions 19 of the wavefront 11 that are convex on the first plane diverge as they propagate toward the second plane 15. The intensity on the second plane 15 is accordingly increased, or reduced, compared to the first plane 13. A measurement of the intensity gradient along the optical axis 21 provides indications of the local wavefront curvature. Looking off the optical axis 21 to obtain information on an extended source can extend this technique, allowing for the use of a resolved object for the correction.

The technology that creates the multiple images is based on local displacement of lines in a diffraction grating used to introduce arbitrary phase shifts into wavefronts diffracted into the non-zero orders, a principle that is well known in the art. For further discussion on this topic, see Blanchard, P. B. and Greenaway, A. H., *Simultaneous multi-plane imaging with a distorted diffraction grating* Applied Optics, 1999. 38: p. 6692-6699, and Otten, L. J., Soliz, P., Greenaway, A. H., Blanchard, M., and Ogawa, G. *3-D Cataract Imaging System*, In *Proc. of 2nd International Workshop of Adaptive Optics for Industry and Medicine,* 1999, Durham, UK, which are hereby incorporated by reference.

A quadratic displacement function is used to alter the optical transfer function associated with each diffraction order such that each order has a different degree of defocus. This modification to produce a distorted grating allows it to serve as a beam splitter while producing simultaneous images of multiple object planes on a single image plane.

A quadratic displacement function is used to alter the optical transfer function associated with each diffraction order such that each order has a different degree of defocus. This 'defocus grating' enables the simultaneous imaging of multiple object planes on a single image plane, using a single camera. The technique preserves the resolution of the input optics in each of the images.

Figure 2:
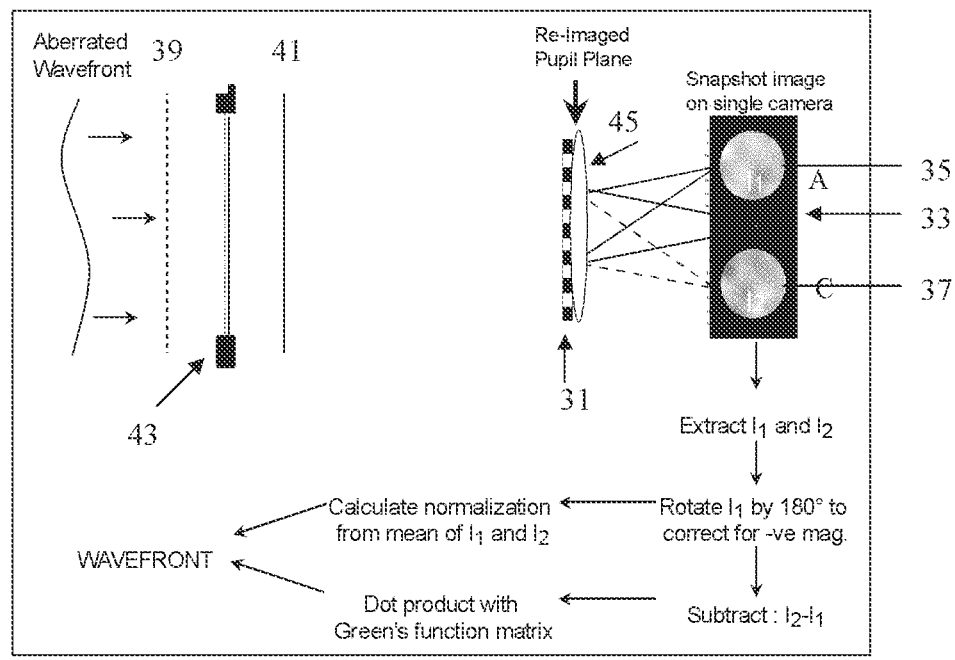
FIG. 2 illustrates the implementation of wavefront curvature sensing using a defocus grating.

In the configuration shown in FIG. 2 grating 31 produces the zero order image 33 (the small white dot in the middle) which records an image of an object at infinity. The two pupil plane images 35 and 37 (I1 and I2) required for wavefront sensing are formed in the −1 and +1 orders. These images correspond to planes 39 and 41 (A & C) equal distances either side of the pupil plane 43 and have magnifications of equal magnitude, but opposite sign. Other orders (e.g., +2, −2) can be used with equal success and offer the opportunity to select the intensity of the signal observed by the detector, an important consideration in a high energy laser application, with high energy being defined by the American National Standards Institute (ANSI).

The ability of the configuration shown in FIG. 2 to provide data suitable for the phase diversity algorithm has been demonstrated by applying a variable amount of defocus to a collimated laser beam. For the example as shown in FIG. 2, a 1.5 cm diameter laser beam (not shown) was placed on distorted grating 31 having a diameter of 1.5 cm, a period of 30 µm and distorted with 60 waves of defocus that had been placed adjacent to a 10 cm focal length imaging lens 45.

Figure 3:
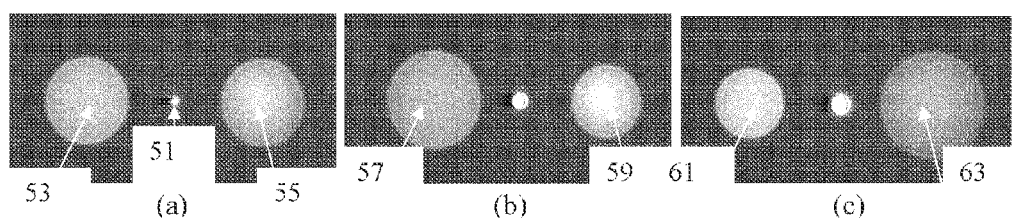
FIGS. 3(a), (b) and (c) illustrate diffraction grating wavefront sensor ("DGWFS") images corresponding to (a) zero, (b) negative, (c) positive defocus.
Figure 4:
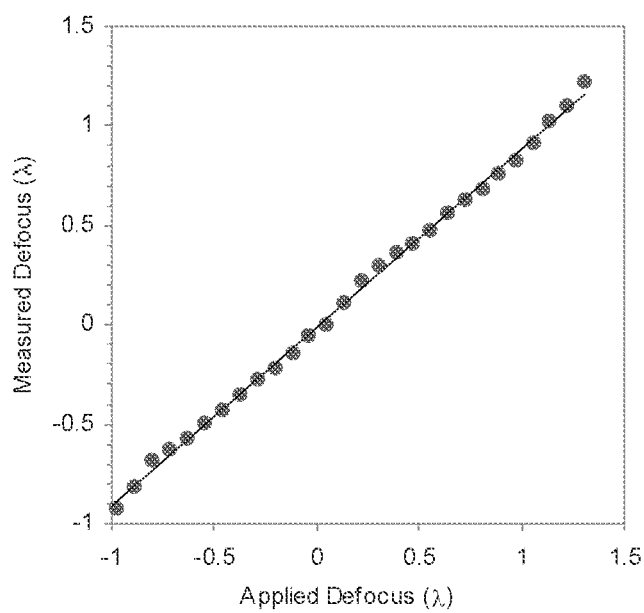
FIG. 4 illustrates the measurement of defocus using the DGWFS technique reflecting the near perfect correlation to the amount of defocus introduced.

With the laser beam accurately collimated (a step that is not necessary for the practicing of the method of the present invention), the image in FIG. 3 was recorded. This shows the focused spot in the zero order 51 and equal size images 53 and 55 of the planes either side of the grating lens combination, FIG. 3(a). When a focus error is applied to the laser beam, the images in the non zero orders change size in opposite but equal amounts, but do not change shape, a feature that is expected in pure defocus, FIG. 3(b) and FIG. 3(c) (images 57, 59, 61 and 63). The phase diversity algorithm subtracts the +1 and −1 image and multiplies the result by a pre-determined matrix using a Green's function analysis to generate the wavefront shape. The algorithm has been shown to be able to accurately measure the amount of defocus (FIG. 4). The ability to measure higher order aberrations and the absence of cross-talk between aberration modes had been demonstrated in simulations and in laboratory experiments at the visible band. See, Otten, L. J., *Measurement of Highly Scintillated Wavefronts with G. Erry, J. Lane, P. Harrison, S. Woods, and M. Roggemannin Proceedings of the 3rd International Workshop on Adaptive Optics for Industry and Medicine*, 2002, Albuquerque, N. Mex.: Ed. S. Restaino and S. Teare, Starline Printing, 2002, 223-240 and Harrison, P., Erry, G. R. G., and Woods, S. C. *A Practical Low Cost Wavefront Sensor with Real Time Analysis presented at 3rd International Workshop on Adaptive Optics for Industry and Medicine.* 2001, Albuquerque, N. Mex., which are hereby incorporated by reference.

Figure 5:
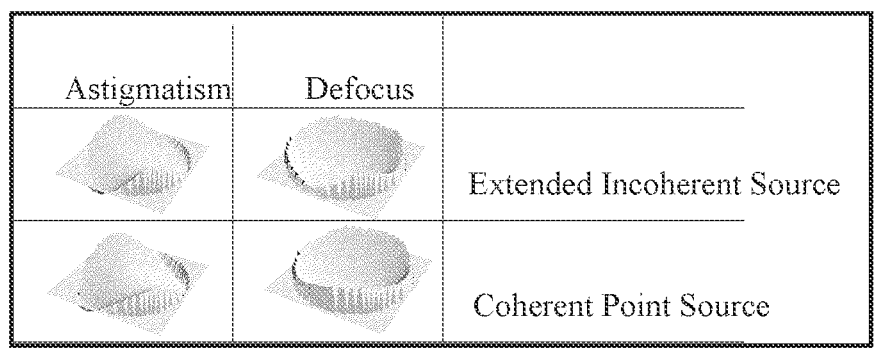
FIG. 5 illustrates a sample of extended source wavefront sensing.

The ability of the DGWFS to work with extended laser sources, when looking at a laser beam in these proposed applications is shown in FIG. 5. The phase map from a point source is compared to the map obtained using an extended object for two static aberrations (6 waves of astigmatism and 3 waves of defocus). The measured phase maps are seen to be very close.

In a wavefront curvature sensor, an aperture stop (shown in later figures) within the optics is used to select that portion of the scene to be used for wavefront sensing. Varying the size of this stop provides a mechanism by means of which the relative contribution within the wavefront sensing from various aberration sources at different locations may be characterized. This provides a unique capability to control the isoplanatic angle, the level of scintillation and the flux levels that contribute to the wavefront sensing system.

Computer simulations showed that the DGWFS continues to work well with extended sources and with substantial scintillation under conditions in which conventional techniques fail. Even with very severe aberrations and an extended scene, only 2-3 iterations of the algorithm are required to achieve an accurate estimate of the wavefront, and in most cases, no iterations are required.

Besides being able to create the needed multiple images simultaneously, the wavefront curvature compensation technique of the present invention requires that the necessary matrix multiplications be performed within the characteristic time scale of the distortion being corrected. The calculation of the phase at each pixel (or mode) is completely independent. All pixels in the input image are used to calculate each mode, so the calculation time is independent of mode complexity. The Green's function matrix used in the analysis (actually 1018 matrices) was designed to calculate the phase at those pixels, however suitable Green's functions could be calculated to yield almost any modes (for example Zernike modes). As all the modes can be calculated independently, the algorithm is highly suited to parallel processing, in which case, given enough parallel processors, any number of modes (up to the resolution of the input image) can be calculated in parallel, significantly reducing the processing time.

As the modal wavefront reconstruction is a simple matrix multiplication, it is eminently suited to a digital signal processing ("DSP") based solution, as such, there is no technical reason why a parallel DSP processing system capable of reconstructing a large number of modes running at 10 kHz could not be used. In fact, using suitable dedicated modern processing, it may be possible to achieve this for a small number of modes using a single processor, assuming the data input bandwidth from the detector is sufficiently fast.

The original analysis had been substantiated with both laboratory demonstrations and an extensive set of measurements under simulated propagation conditions. For further discussion on this, see Otten, L. J., Lane, J., Erry, G., Harrison, P., and Kansky, J. *A comparison between a Shack-Hartmann and a Distorted Grating Wavefront Sensor under Scintillated Propagation Conditions in Conference on Optics in Atmospheric Propagation and Adaptive Optics Systems,* 2002, Crete, Greece: SPIE, which are incorporated by reference.

Figure 6:
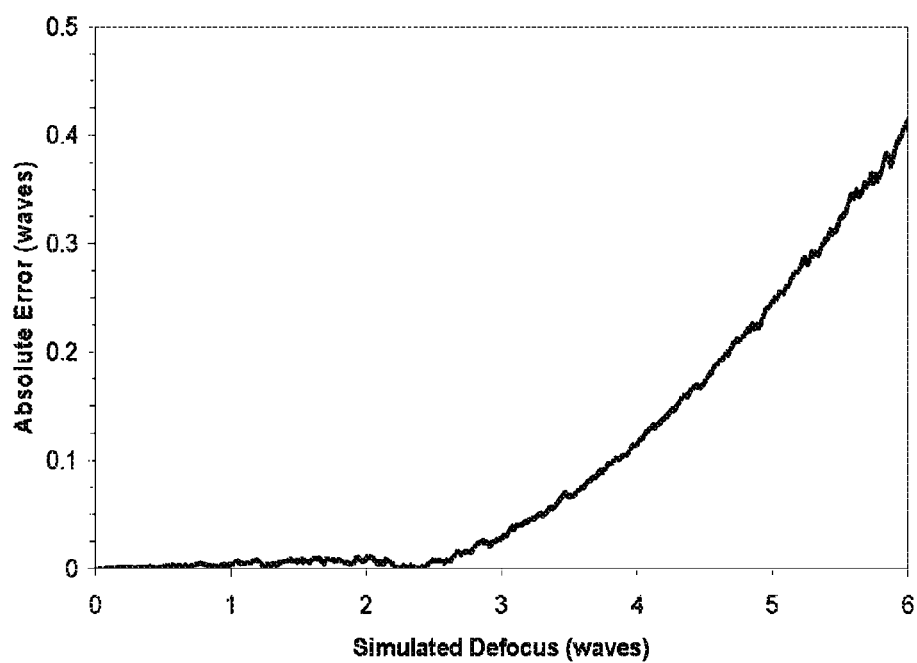
FIG. 6 illustrates the simulated wavefront sensor performance.

An analytical model of the wavefront sensor was produced and used to estimate the dynamic range and sensitivity of a representative system. To ensure that the model was valid, the simulated data was processed using the normal data reduction application. This analysis suggested that this infrared wavefront sensor would be linear up to an error of approximately 2.5 waves (at a wavelength of 3.39 µm). The system would then become nonlinear (but predictably so) up to approximately 10 waves of error. The sensitivity of the system was predicted to be substantially better than $\lambda/100$ throughout this range, with a sensitivity of better than $\lambda/1000$ at low (less than one wave) levels of distortion. The results of this modelling are shown in FIG. 6. Similar modelling has created systems with over +/−70 waves of dynamic range with $\frac{1}{10}$ wave sensitivity.

Figure 7:
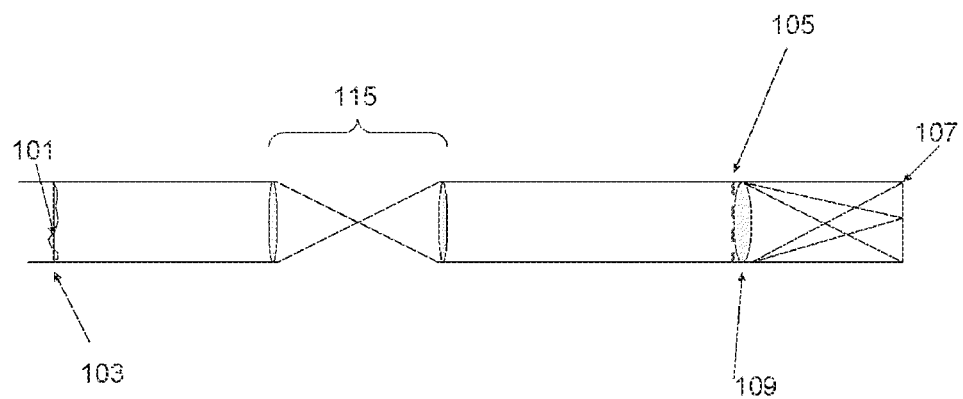
FIG. 7 illustrates the generic components required to practice the method of the present invention.

FIG. 7 illustrates the components used to practice the method of the present invention. A wavefront 101 to be measured is directed onto pupil plane 103, the wavefront at pupil plane 103 is then redirected onto grating 105, modifying wavefront 101, which modified wavefront, is subsequently focused onto detector 107 through lens 109. Optional pupil relay and magnification optics 115 can be used to orient and resize wavefront 101 as required by the application being used.

Figure 8:
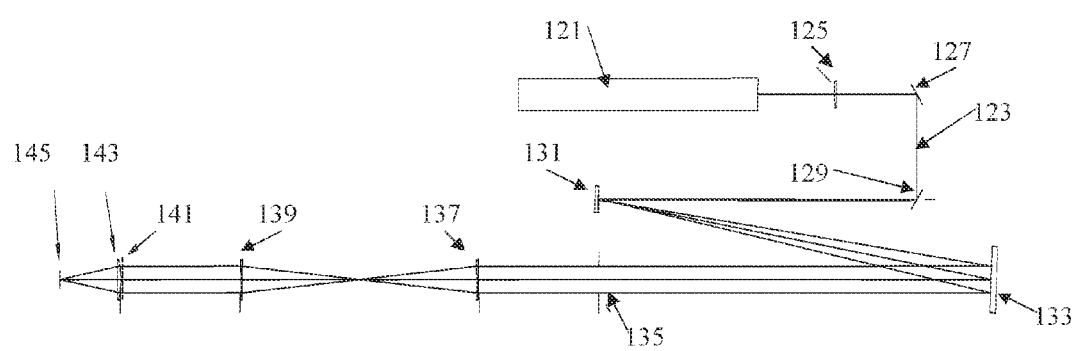
FIG. 8 illustrates an alternative optical layout showing the details of the various lens and beam splitters required.

A detailed design of the layout for a laboratory wavefront measurement device is shown in FIG. 8. This is only an example of one application that can be used with the infrared wavefront sensing technique of the present invention and is not intended to limit the method of the present invention.

As stated above, FIG. 8 represents an actual set up for a specific application, and is provided only for the purposes of illustration and is not intended to narrow the scope of the invention beyond what has been described with reference to FIG. 7 above.

With reference to FIG. 8, laser 121 generates light beam 123 which is passed through attenuator 125 and is re-directed using optics 127 and 129. Mirrors 131 and 133 are used to disperse and re-collimate beam 123 which is then directed through aperture 135 (collimation is not required for the functioning of the method of the present invention). It is the wavefront as it exists at aperture 135 that will ultimately be imaged onto detector 145. Beam 123 is subsequently directed through lenses 137 and 139 which are used to position and magnify beam 123. Lenses, for example, can be, but are not limited to 200 mm F1 CaF2 lenses, but can be any conventional optics used for optical relay and magnification and whose selection will depend on the application for which the system of the present invention is being used. Beam 123 is then passed through diffraction grating 141 before being focused by lens 143 onto the focal plane of detector (infrared camera) 145. Lens 143, can be but is not limited to a 100 mm F1 CaF2 lens and must only serve to focus the beam 123 as modified by grating 141 onto a detector 145, in this case an Infrared camera.

The basic optical design parameters for the example laser wavefront diagnostic ground test optical system as shown in FIG. 8 above are:

Resolution: λ/100
Dynamic Range: >4λ focus
Temporal Resolution: 30 Hz
HEL Power Capability: >10 KW
Order Definition: >First 20 Zernike terms These design parameters will change significantly depending on the application for which the method of the present invention is being used.

A custom AR coating can to be applied to all optics to reduce ghosting and improve transmission at wavelength being sampled. A beam dump (not shown) can also be included for the purposes of terminating the unwanted radiation transmitted by the beam splitter and as a thermal background source since it can be placed in a pupil plane of the imager.

In one embodiment of the invention, the grating 141 substrate is constructed with $SiO_2$ or IR grade fused silica substrates. However, other suitable substrate materials can be used.

Figure 9:
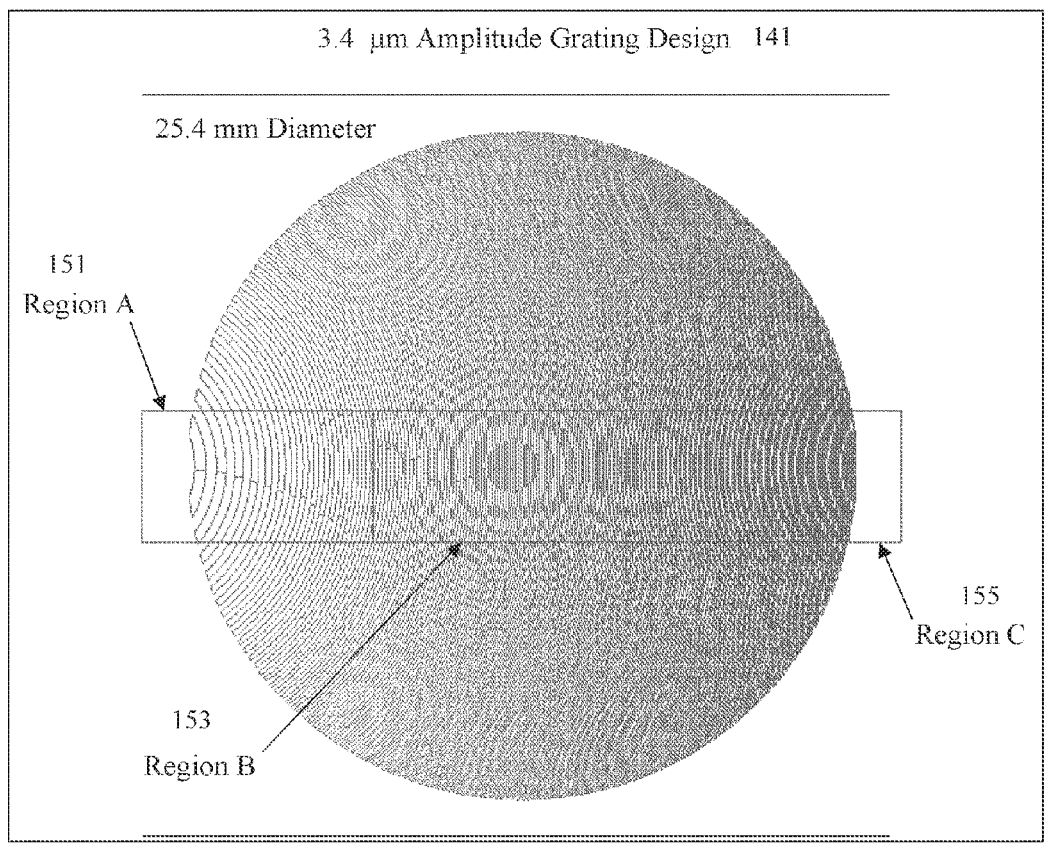
FIG. 9 illustrates an example of the grating design.
Figure 10:
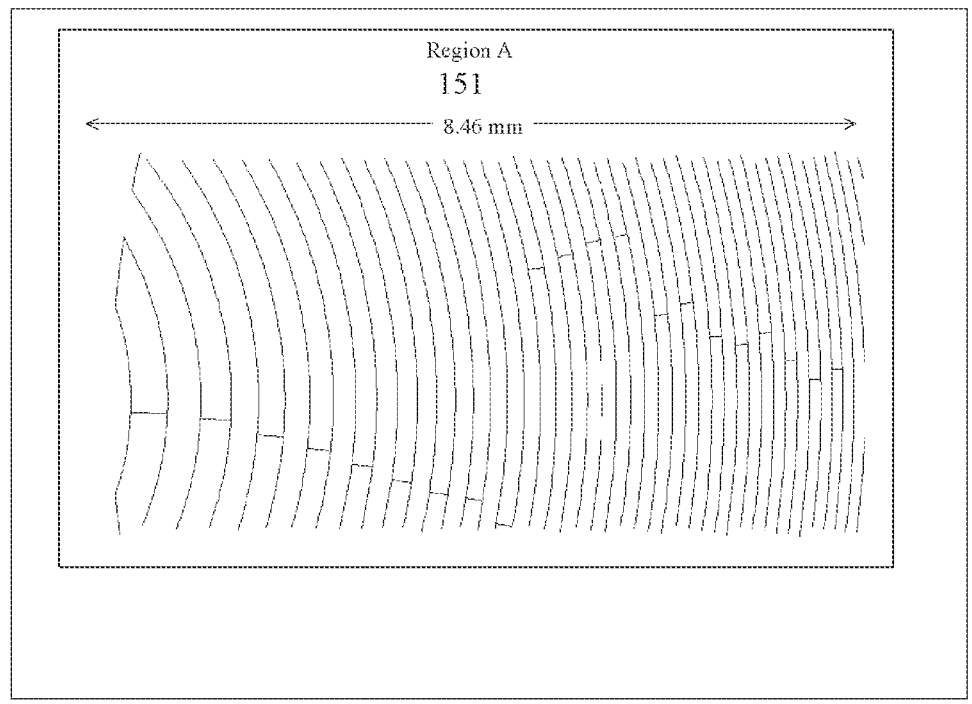
FIG. 10 illustrates the left side of the grating design.
Figure 11:
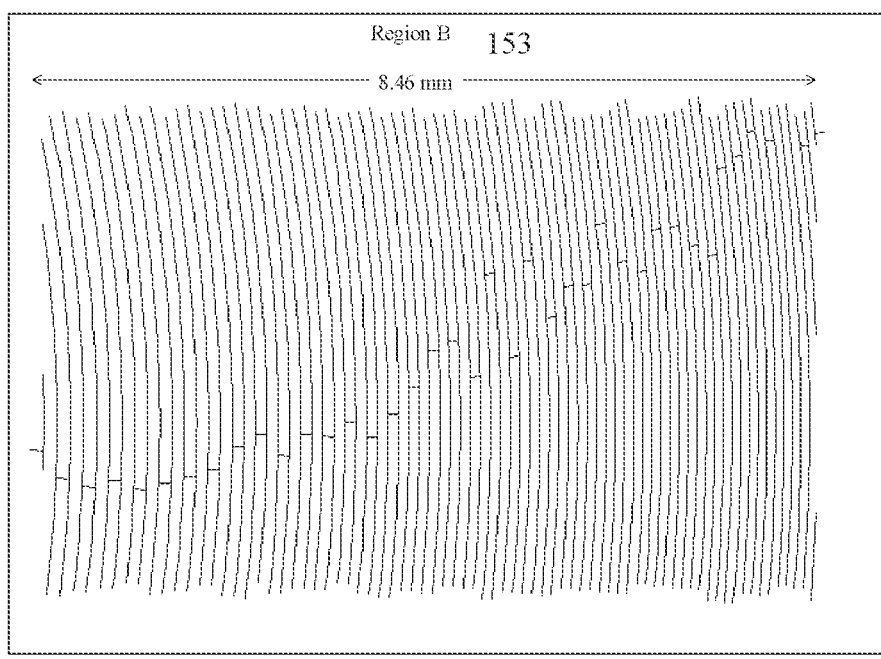
FIG. 11 illustrates the center of the grating design
Figure 12:
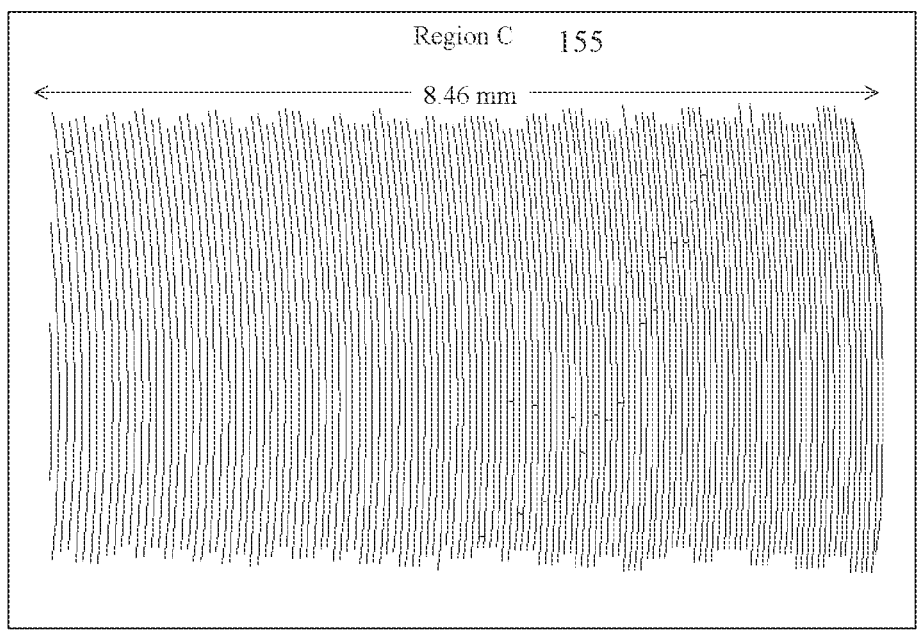
FIG. 12 illustrates the right side of the grating design

The design for grating 141 is shown in FIG. 9 where the overall layout for a 2.54 cm diameter grating 141 is noted. This is an example design for grating 105, as shown in FIG. 7, as implemented in the actual laboratory set as shown in FIG. 8. FIG. 10, FIG. 11, and FIG. 12 are sections 151, 153, and 155 of grating 141 taken across its diameter to illustrate how the grating spacing changes. These sections are all of the same size. (The rather unusual features on the drawings are an artifact of the printing. The grating lines are actually arcs of concentric circles of varying spacing and width.)

Figure 13:
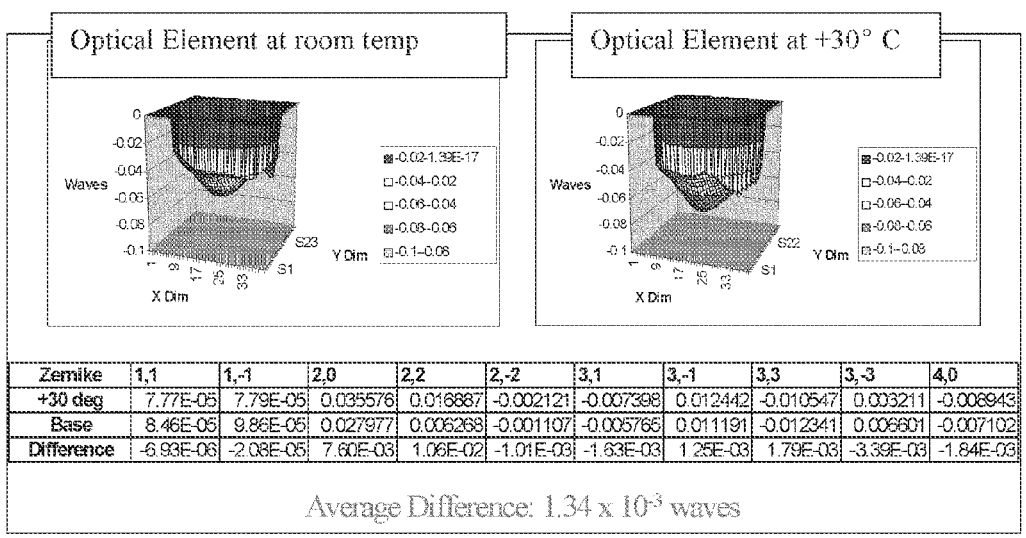
FIG. 13 illustrates the change in wavefront (in waves) for a 30° C. increase in the temperature of an optical element.
Figure 14:
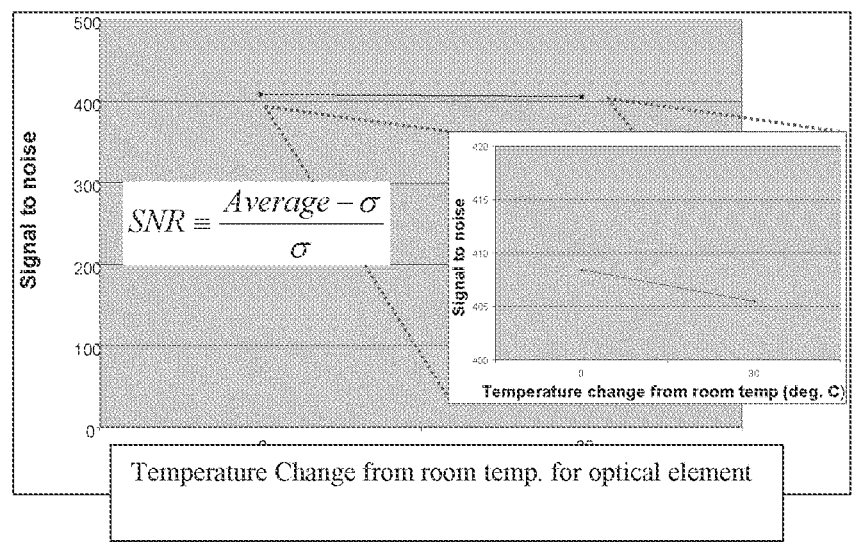
FIG. 14 illustrates the change in SNR as the temperature of an optical element is changed, and further illustrates that the insert is an enlargement of the curve to illustrate the small decrease as temperature is increased.

The signal to noise (SNR) for the sensor is measured using the following:

$$SNR = \frac{(\text{Average} - \sigma)}{\sigma}$$

where the averages and standard deviations, σ, were determined using a 50 wavefront data set. The change in the measured wavefronts for an amplitude grating imposed by an optical element that is 30 deg C hotter than ambient condition is shown in FIG. 13. Note that the average change is about λ/1000. The change in the SNR as the mirror is heated reflects this very small influence of increased background temperature, FIG. 14. This indicates the advantages of the approach of the present invention which depends on a differencing technique that virtually eliminates any systematic thermal effects, a result that is critical to uses at high flux levels.

Figure 15:
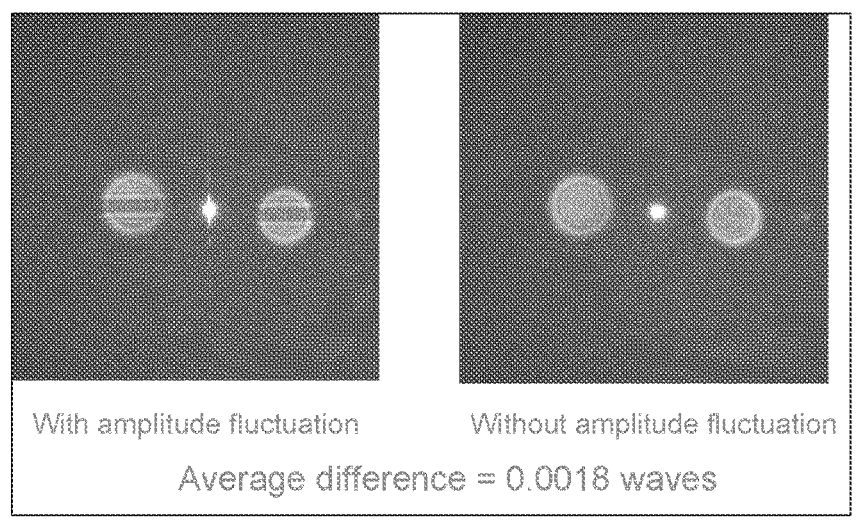
FIG. 15 illustrates the raw images of an obscured beam (left) and normal beam sample (right).

The robustness of the present invention to the presence of an obscuration in the sampled beam such as might be introduced by a secondary spider mount has also been shown. Within the laboratory set up of the present invention, a black cylindrical object can be placed across the collimated beam to introduce an obscuration. The resulting raw images are shown in FIG. 15. This change introduced less than 0.018 waves of distortion indicating that the sensor retains its robustness to large vignetting of the beam, such as might be introduced in a hole coupled output beam.

Figure 16:
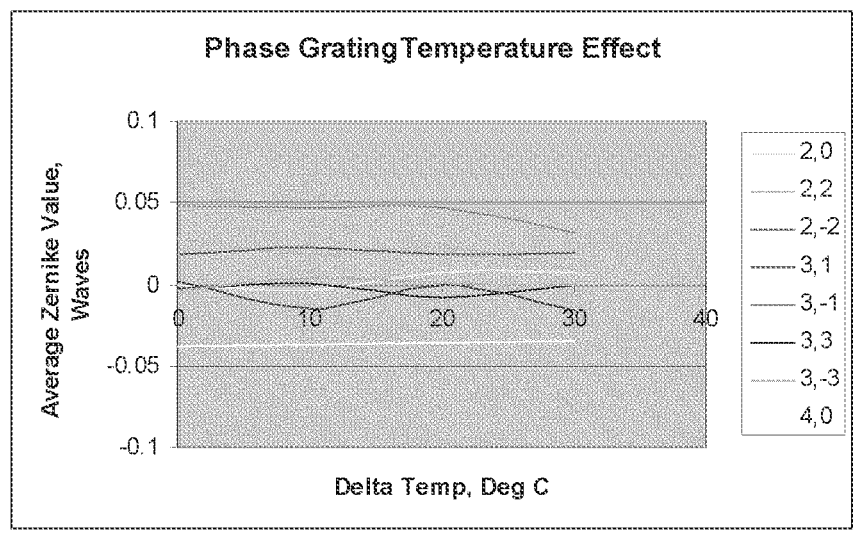
FIG. 16 illustrates the background temperature effect.

Grating 141 possesses the same insensitivity to changes in the background temperature as in the grating previously described. The same technique employed in the amplitude grating temperature data was used with a relay mirror being heated up to 30° C. above ambient. The effect on the recovered wavefront was again within the noise of the measurement. See FIG. 16. With an uncertainty of about 0.02 waves, these data show no noticeable effect of changing the background temperature, indicating that phase grating 141 (shown in previous figures) exhibits the same insensitivity to background temperature as the amplitude gratings. As with the amplitude gratings, these results are very important to high power application where the optical elements increase in temperature due to the higher flux levels.

Figure 17:
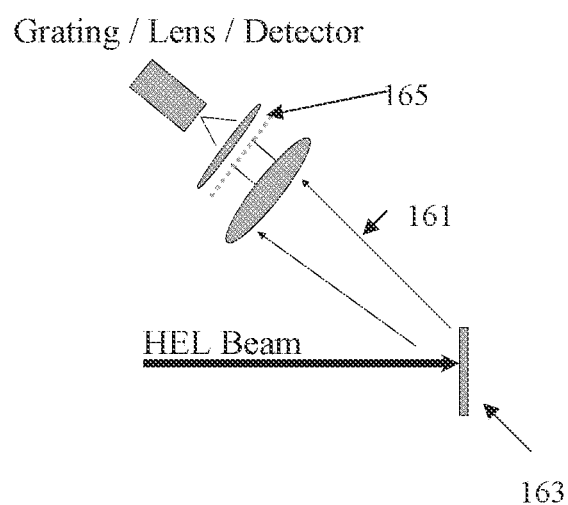
FIG. 17 illustrates the wavefront based on a scattered light source.

There are several alternative approaches to implementing a high power version of the laser sensor employing the technology described above are discussed next. The first approach uses the reflected light 161 from an existing optical element 163 as the sample source, FIG. 17. This has several advantages. First the sensor is not intrusive, requiring no changes to the facility optical train. The wavefront sensor is an all refractive design, including the grating element 165, making it similar to the above described system and tests. Because the input to the sensor is from a low power source, the entire optical train can be made of low power, low cost elements.

Figure 18:
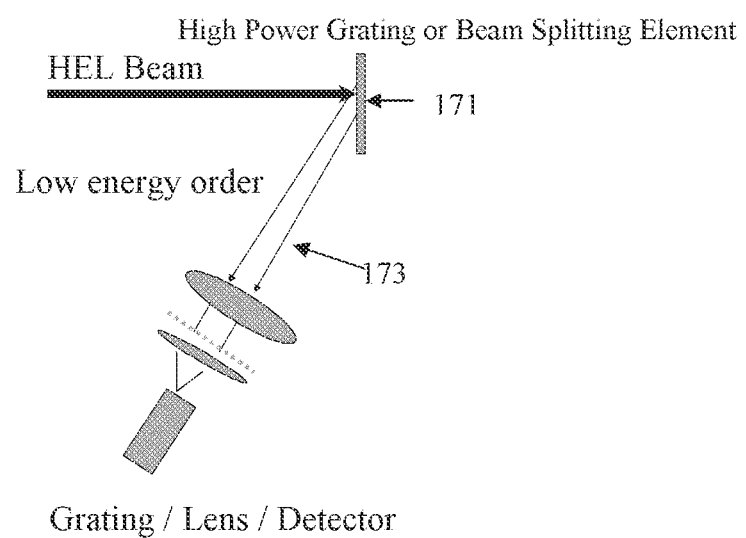
FIG. 18 illustrates the in place grating.

The second approach uses an existing grating or beam splitting element 171 in the laser optical train to provide a sample 173, FIG. 18. By relaying one of the unused higher order outputs, this continues to be non intrusive and provides an accurate representation of the wavefront. The sample continues to be low power and can use transmission gratings making it the same as the above described tests. This does, require that there be a linear sampling.

Figure 19:
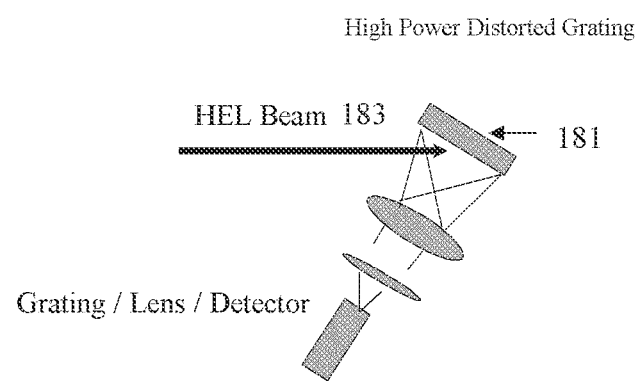
FIG. 19 illustrates direct sampling.

The last approach, shown in FIG. 19 inserts a high power distorted grating 181 directly into a sample of beam 183. This provides a true sampling of the laser wavefront. It does however introduce the need to handle the full power and requires a high power distorted reflecting grating.

In the design of such systems, it must be determined whether a reflective or a refractive grating should be used. While they can both employ the grating design tools previously developed, and are both suited to using conventional ray tracing optical design software such as that offered under the trademark Zemax, they do have differing levels of risk and application implications. Using a refractive requires that there be a suitable low power sample of the laser output which may be a limit to the eventual employment of the technology in future very high power applications. The alternative design concept requires the development of a technique that can lay down a distorted phase grating on a substrate suitable for high surface fluxes. Making gratings on reflecting surfaces for use in high power is known within the art. To prior art gratings have all been either linear rulings or are linear designs using an etching process that produces an amplitude grating.

For the remainder of the optical design, reflective and refractive optics are used. A beam relay and resizing assembly are needed to re-image the entrance pupil plane at the front surface of the distorted grating. The same relay sets the beam diameter at the grating to the correct size. An objective lens images the two grating orders on the detector focal plane sufficiently far apart so that they do not overlap at the maximum focus aberration expected. In addition to these basic requirements a field stop to reduce stray light from entering the sensor, usually placed at the focus of the beam-resizing segment is needed. Depending on the grating approach selected the relay optics will be different. The most obvious difference is that with the reflective grating the orders are directed away from the optical axis. This requires that they be captured and brought together at the detector to avoid having to use two cameras.

Figure 20:
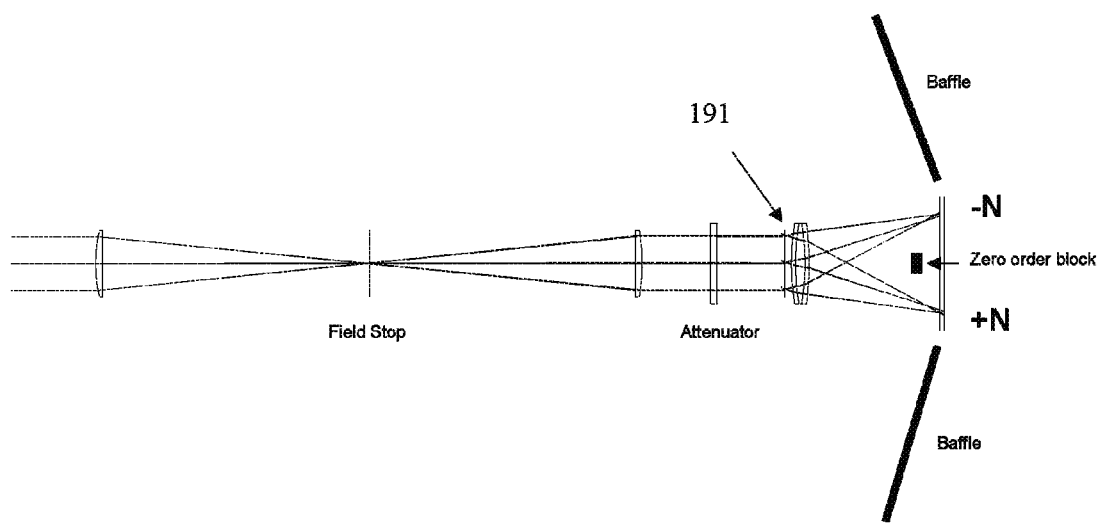
FIG. 20 illustrates an optical layout for the refractive grating.
Figure 21:
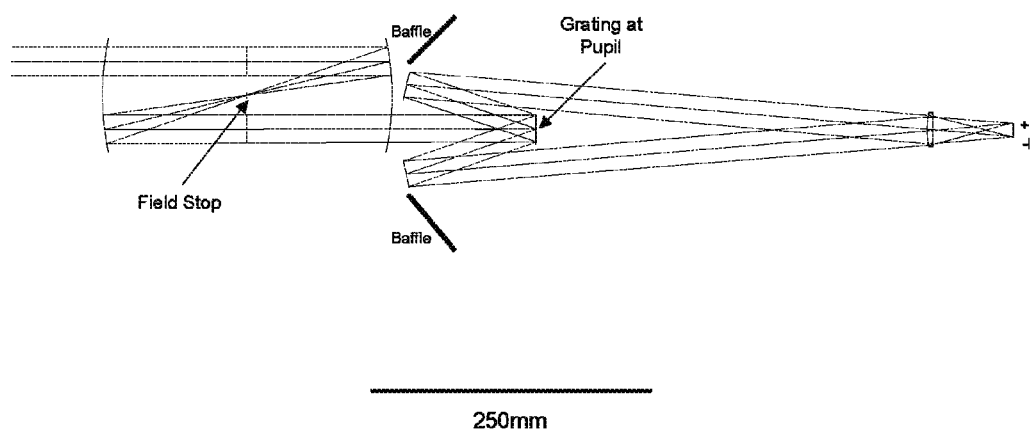
FIG. 21 illustrates a proposed optical layout for the reflective grating.

FIG. 20 and FIG. 21 show a general layout for a design of the optical system. FIG. 20 is for the refractive grating 191 and FIG. 21 is the reflective grating 193. Not shown is the pick off of the laser beam.

All optics can be AR coated over the appropriate band and use appropriate substrates for the refractive optics (e.g. quartz or glass) and for the reflective components (e.g. low expansion glass or aluminum).

Design of the distorted grating and camera selection are considered critical elements. A diffractive element (combining the dual role of beam splitter and defocus) is achieved by encoding a quadratic phase shift into a grating using the detour phase approach. The grating is distorted according to, $$\Delta_x(x, y) = \frac{W_{20} d}{\lambda R^2}(x^2 + y^2)$$

where $\lambda$ is the optical wavelength, x and y are Cartesian co-ordinates with an origin on the optical axis and R is the radius of the grating aperture centered on the optical axis. The parameter $W_{20}$ is the standard coefficient of defocus equivalent to the extra path length introduced at the edge of the aperture; in this case for the wavefront diffracted into the +1 order.

The phase change ($\phi_m$) imposed on the wavefront diffracted into each order is given by, $$\phi_m(x, y) = m \frac{2\pi W_{20}}{\lambda R^2}(x^2 + y^2)$$

Figure 22:
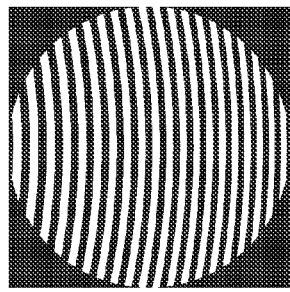
FIGS. 22(a) and 22(b) illustrate gratings distorted according to equation describing $\Delta_x(x,y)$, with R=20d having the grating origin (0,0) being at the center of the circular aperture; (a) $W_{20}=1\lambda$, and (b) $W_{20}=3\lambda$.
Figure 22:
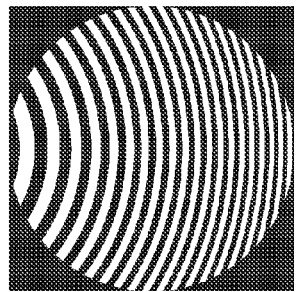

Examples of gratings distorted according to the above equation with R=20d and the grating origin (0,0) being at the center of the circle aperture are shown in FIG. 22, FIG. 22(a) having a $W_{20}$ value of $1\lambda$, and FIG. 22(b) having a $W_{20}$ value of $3\lambda$. As the level of defocus increases, the curvature of the grating lines increases and it becomes apparent that the grating lines are arcs of circles. This can be seen more clearly by considering the equation of the grating lines themselves, $$\frac{x}{d_0} + \frac{W_{20}(x^2 + y^2)}{\lambda R^2} = n$$

where we now refer to $d_0$ as the grating period at the aperture center, the integer values of n define the loci of each grating line, and n=0 corresponds to a grating line passing through the mask center. The first term in this equation represents the undistorted grating and the second term encodes the quadratic distortion. With straightforward algebraic manipulation, it can be shown that this equation represents circles centered at, $$x_n = \frac{\lambda R^2}{2 W_{20} d_0}$$

with radii $C_n$ given by, $$C_n = \sqrt{\frac{n \lambda R^2}{W_{20}} + \left(\frac{\lambda R^2}{2 d_0 W_{20}}\right)^2}$$

Ignoring the second term, which is a constant offset, we see that $C_n$ is proportional to $n^{1/2}$.

The grating period at the center of the mask ($d_0$) is the most characteristic period to quote because it defines the diffraction angles to the centers of the images in the non-zero orders. However, the grating period across the aperture is not constant (see FIG. 22). Considering the grating structure along the x-axis, at a distance $x_0$ from the origin, the grating period (d) is given by, $$d = \frac{d_0 \lambda R^2}{\lambda R^2 - 2 d_0 W_{20} x_0}$$

Note that the variation in fringe period across the grating is dependent on $W_{20}$, while the period at the center of the grating ($x_0$=0) is independent of $W_{20}$. From this equation with $x_0$=−R, the minimum grating period ($d_{min}$) is given by, $$d_{min} = \frac{d_0 \lambda R}{\lambda R + 2 d_0 W_{20}}$$

This will determine the accuracy required in grating fabrication.

The quadratic phase function imparts a phase delay on wavefronts scattered into the non-zero diffraction orders resulting in an altered wavefront curvature. The grating, therefore, has focusing power in the non-zero orders, and an equivalent focal length ($f_m$) can be calculated for these orders, $$f_m = \frac{R^2}{2 m W_{20}}$$

where R is the grating radius and $mW_{20}$ is the path length difference introduced at the edge of the aperture in the mth diffraction order. A single quadratically distorted grating thus acts as a set of lenses of positive, neutral and negative power.

In practice, it is more useful to implement such a grating in close proximity to a lens, with the lens providing the majority of the focusing power and the grating effectively modifying the focal length of the lens. When a quadratically-distorted grating is placed in contact with a lens of focal length f, the focal length of the combination in each diffraction order (using the thin lens approximation) is given by, $$f_m = \frac{fR^2}{R^2 + 2fmW_{20}}$$

It is preferred to use the grating in conjunction with a single refractive achromatic lens. However, the grating can, in principle, be positioned anywhere within a multi-element optical system. The exact effect of using the grating (within a compound optical system) may be found from standard formulas for such systems and with the grating replaced by a lens of appropriate optical power for the diffraction order considered and placed in the plane of the grating. This implementation may be important in retro fitting an existing wavefront sensor design, but based on obtaining sufficiently high optical quality using standard acromats, will be avoided in the preferred embodiment.

The distance, $\delta z_m$, from the object or image plane in the mth order to that in the zero order, is given by $$\delta z_m = -\frac{2mz^2 W_{20}}{R^2 + 2mzW_{20}},$$

where z is the distance from the central object/image plane to the primary/secondary principle plane of the optical system. In general, the plane separation between each pair of adjacent orders will not be equal. However, in the case where $2mzW_{20} \ll R^2$, which can be approximated by, $$\delta z_m \approx -2m\left(\frac{z}{R}\right)^2 W_{20}$$

the planes are symmetrically spaced. The spacing, $\delta z_m$, along with the desired wavefront resolution, is also used to determine the detector size. For the present use, re-imaging will be conducted as necessary to obtain a fill factor of slightly less than 100% for the grating.

The level of alignment tolerances is quite modest for these types of sensors. Unlike Shack-Hartman sensors, where the alignment of the individual images is critical, any alignment errors can be easily removed via software in a DG WFS sensor. In practice, alignment errors may lead to an offset of the grating position; hence the effect on performance of an off-axis quadratic distortion should be considered. An analysis of the alignment errors follows.

If the origin of the quadratic function is $(x_o, y_o)$ the phase change imparted on the wavefronts scattered into each diffraction order becomes, $$\phi_m(x, y) = \frac{2m\pi W_{20}}{\lambda R^2}[(x - x_o)^2 + (y - y_o)^2]$$

which can be expanded to give, $$\phi_m(x, y) = \frac{2m\pi W_{20}}{\lambda R^2}[(x^2 + y^2) - 2x_0 x - 2y_0 y + (x_0^2 + y_0^2)],$$

where the x and y axis are as defined earlier.

The first term in this equation is the defocus term obtained when the quadratic function is centered on the optical axis. The level of defocus and hence, position of planes being imaged, is not therefore dependent on the grating position in the x-y plane.

The second and third terms in the equation represent linear increases in phase across the x and y-axes of the grating plane respectively. This phase tilt has the effect of changing the positions of the diffraction orders, while leaving the position of the zero order (m=0) and level of defocus unchanged. Through choice of $x_0$ and $y_0$, the position of a particular diffraction order in the image plane can be controlled. The fourth term in the equation is simply a constant phase offset and does not affect the image quality. In general, measurement accuracy will increase with plane separation and aperture diameter, while the magnitude of measurable wavefront distortions will decrease. A trade-off between measurement accuracy and dynamic range is required to meet the system parameters suitable for each application.

In selecting the detector for the laser wavefront sensor there are several competing requirements. First, the spectral band of the wavefront requires a detector sensitive to the radiation. The second requirement is that it be able to operate at reasonable frame rates to measure any temporal variations. 30 frames per second is sufficient, although a much faster rate may be required for any active control loop application. The camera has to be of the frame transfer type to allow it to provide a snap shop of the intensity patterns. Next, to achieve the desired resolution, a minimum number of elements are required. And last, the sensor needs to have a high quantum efficiency at the appropriate wavelength.

Figure 23:
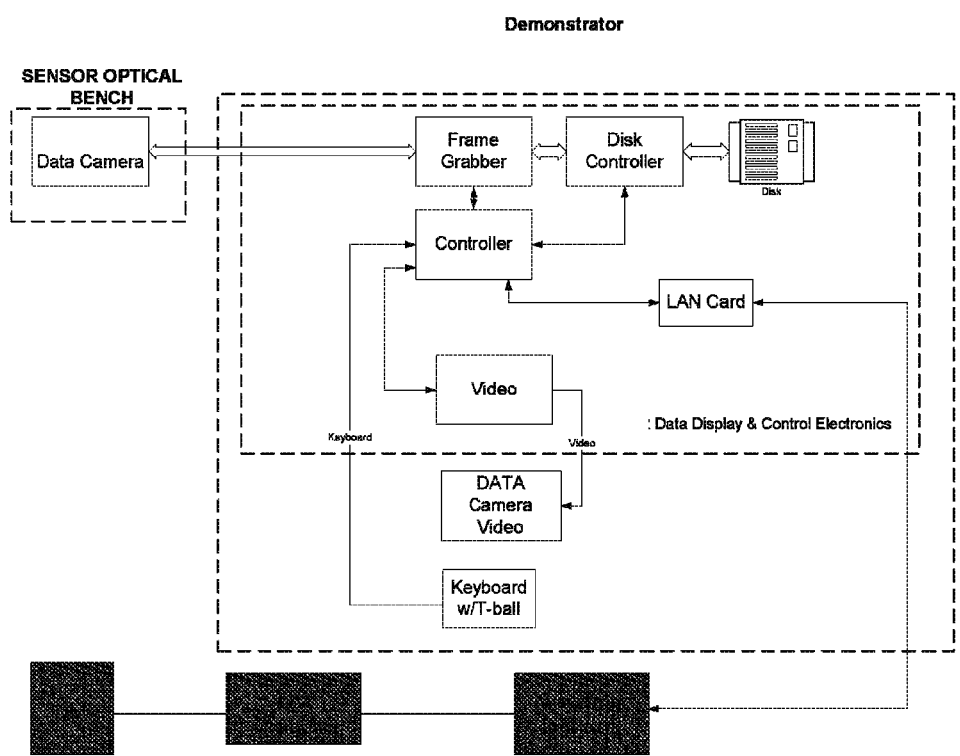
FIG. 23 illustrates the basic system component layout for a closed loop system.

Overall data management for the laser wavefront diagnostic sensor requires several distinct subsystems: a camera interface and manager, a data processor and the storage media. Shown schematically in FIG. 23 is an architecture that has been implemented several times and proven to be both effective and robust in laboratory and field applications. The imaging system consists of a sensor with an independent imager data interface to control the camera, store the data, and display the output for alignment and testing. Camera raw data is simultaneously transferred to RAM/disk and displayed on the monitor to be used by the operator for camera control and to verify that the correct data are acquired. Batch processing of longer test data sets can be done off line using an existing batch processing tool.

The data analysis software first loads an image from the data camera. This is an uncompressed 8, 10, 12 or 16 bit greyscale bitmap. The image format in the software accepts data produced by the camera with almost any pixel size, resolution, and dynamic range.

Figure 24:
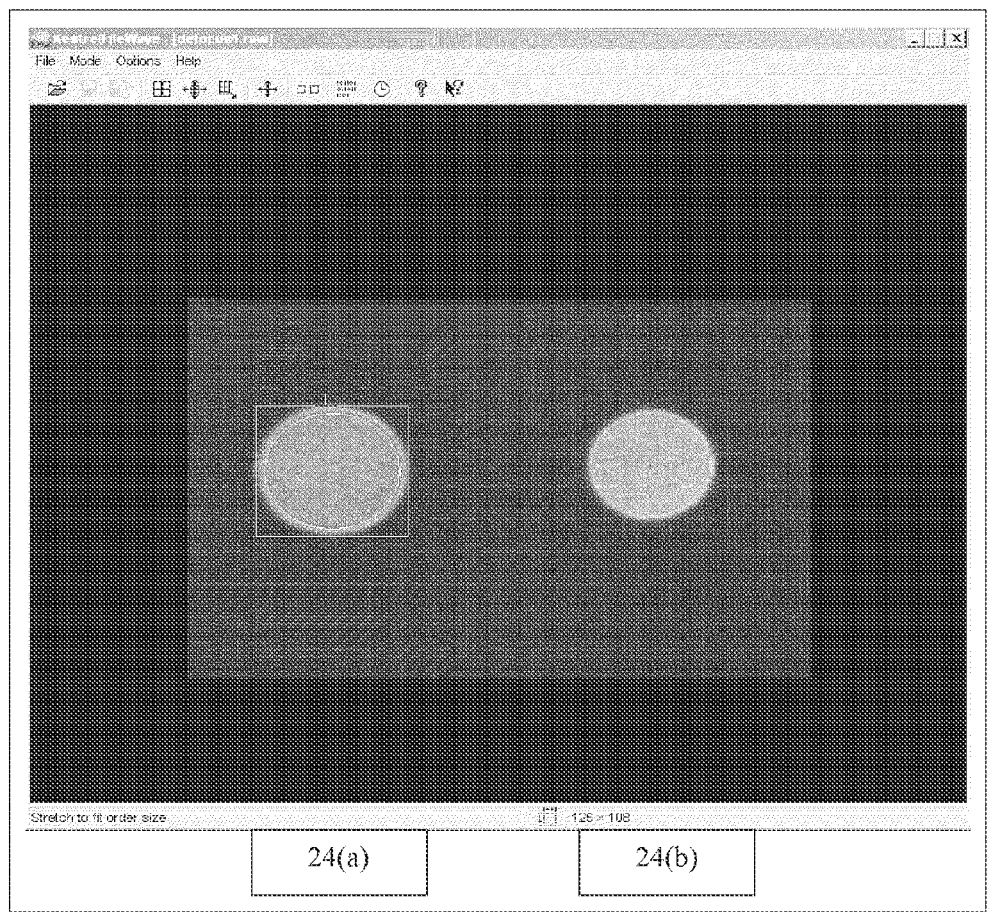
FIGS. 24(a) and 24(b) illustrate full calibration, order sizing with a defocused wavefront.

On loading an image for the first time the program entered Full Calibration mode, where the location and size of the orders is determined. It is assumed that left and right orders are the same size, which will be the case unless there are serious problems with the optical set-up of the system resulting in a differential magnification. An example of the type of data used, order size and location with a defocused wavefront, is shown in FIGS. 24(a) and 24(b). Notice that the left order is now somewhat larger than the right hand order, so the true pupil diameter is equidistant between the two diameters. Hence the ellipse in 24(a) is slightly smaller than the left order diameter and the ellipse in 24(b) is larger than the right order diameter by an equal amount. A similar technique can be used to determine the order size when other aberrations are present.

After the data are identified, processing of the image to obtain the wavefront is started. The first stage is to resample the orders, as selected in the calibration process. The images are resampled to a selectable size, with a pupil diameter as appropriate and the CCD pixel aspect ratio is corrected to give square pixels in the resampled images. If any part of either resampled image is saturated, then the pixels concerned will be noted. It is important to ensure the images are not saturated, as this will give incorrect results.

The second processing stage is to take the difference between the two orders. This stage includes a background subtraction and a 180° rotation for the second image to accommodate the reversal introduced by the diffraction grating.

The third stage is to calculate the wavefront itself. The normalized difference is multiplied by the Green's function matrix loaded on initialization. The resulting phase is then multiplied by a scaling factor to get the correct result in waves, the scaling factor determined by several parameters of the optical system, some of which may be changed by the user. The wavefront is shown as a phase map with a scale shown immediately below. See FIG. 25. Note that the wavefront is only calculated within the pixel diameter region, as the wavefront must have a phase of 0 outside that region (as defined in the boundary conditions of the Green's function used). The display of the wavefront can be customized as required.

The wavefront is displayed as a two dimensional map and in Zernike modes. These may be displayed in the form of a bar chart. See FIG. 25. Note that the first Zernike mode 0,0 (piston) is not shown as this is a measure of absolute phase and has no physical meaning in this context. The Zernike mode display can be customized as required and the calculated modes can also be used to modify the wavefront display and output. When an image has been processed, the resulting wavefront can be saved to disk in one of several formats.

The analysis tool provides display and file output option modifications. Changes in the various physical parameters of the optical system such as the pupil diameter, wavelength of light used, and binarising coefficient can be changed. All parameters can be set by the user as appropriate.

Figure 25:
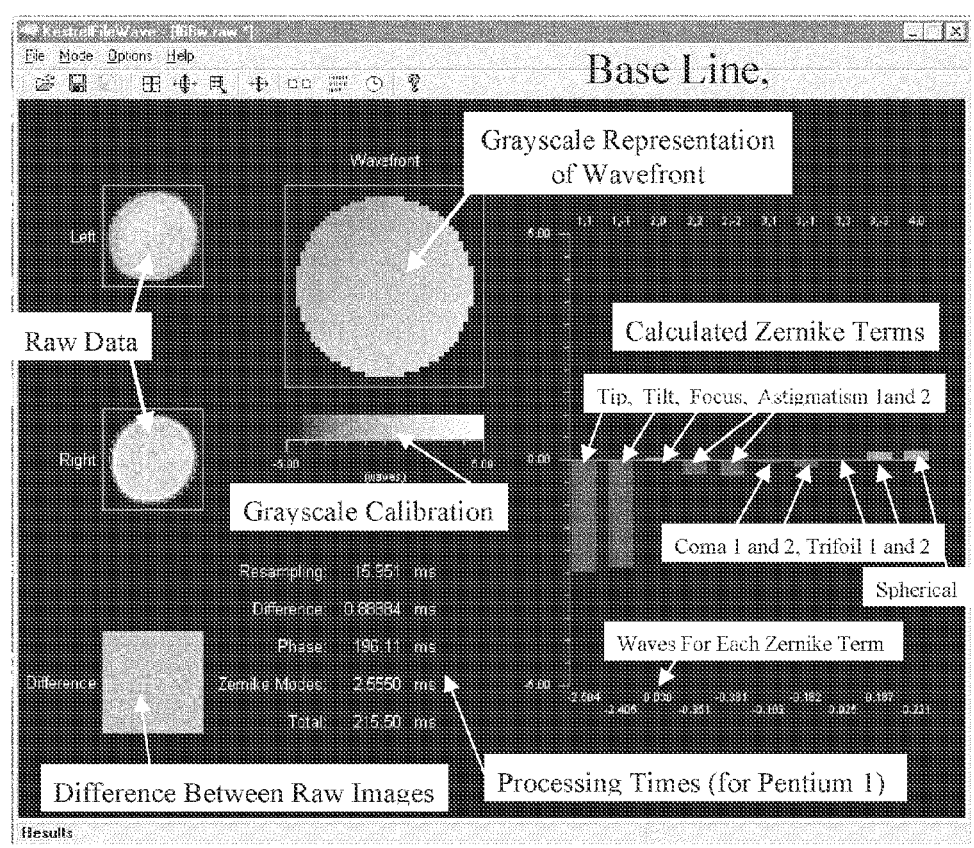
FIG. 25 illustrates an example of baseline data with no added distortions.

The output from the data processing may be presented as a graphics representation. FIG. 25 shows a sample graphics screen that can be used to present the processed data. The figure is annotated to show where the various values are located on the screen. The data in FIG. 25 are for the baseline optical setup, without any known aberrations inserted. These residual errors can be removed by subtracting them from the measurements.

The analysis program allows the automatic processing of large data sets. Two techniques were written into the batch processing routines. This keeps the regions of interest fixed. This works well for data where there is little translation, i.e., tip/tilt on the sampled beam. The second technique automatically determines the location of the region of interest by calculating the centroid of the data and using that to locate the ROI. This process is done for every frame of data which allows the software to process signals with large tip tilt terms. The software allows many thousands of frames of data to be processed automatically and will provide both the wavefront for each time frame, plus an averaged set of statistics for the full data set. The time resolved samples are useful for applying various statistical processes and Fourier analysis to look for time varying signal characteristics.

Physically, the data manager and data processing hardware consists of a single computer with a screen and keyboard interface.

Whereas the drawings and accompanying description have shown and described the preferred embodiments, it should be apparent to those skilled in the art that various changes may be made in the form of the invention without affecting the scope thereof.

We claim:

1. A method of determining the characteristics of a wavefront of a beam of light, said method including the steps of:
   a passing said beam through an optical system, said optical system including relay and magnification optics, a distorted grating, a lens and a detector, said optical system having a pupil plane;
   b positioning said pupil plane on said grating with said relay and magnification optics;
   c using said grating to produce a plurality of images;
   d determining, from said plurality of images, said wavefront; and
   e analyzing said wavefront which as passed through said relay and magnification optics, said grating and said lens for features that characterize said wavefront.

2. The method as set forth in claim 1, of wherein said plurality of images are the at least two diffraction orders of said distorted grating.

3. The method as set forth in claim 1, wherein said wavefront is determined mathematically by the use of said plurality of images, and a Green's function which is a solution to the Intensity Transport Equation.

4. The method set forth in claim 1 wherein said step of using said grating comprises the step of reflecting said beam off said grating.

5. The method set forth in claim 1 wherein said step of using said grating comprises the step of refracting said beam through said grating.

6. The method set forth in claim 1 wherein said beam is direct.

7. The method set forth in claim 1 wherein said beam is scattered.

8. The method set forth in claim 1 wherein said beam is sampled from a direct source.

9. The method as set forth in claim 1, further including the step of collimating said beam by said relay and magnification optics.

* * * * *